United States Patent [19]

Blahak et al.

[11] 4,348,536
[45] Sep. 7, 1982

[54] ODORLESS CATALYSTS FOR THE SYNTHESIS OF POLYURETHANES

[75] Inventors: Johannes Blahak, Cologne; Hans Hübner, Katzenellenbogen; Johannes Koster, Dormagen; Hans J. Meiners, Leverkusen-Schlebusch; Heinz Thomas, Leverkusen, all of Fed. Rep. of Germany

[73] Assignee: Bayer Aktiengesellschaft, Leverkusen, Fed. Rep. of Germany

[21] Appl. No.: 875,278

[22] Filed: Feb. 6, 1978

[30] Foreign Application Priority Data

May 28, 1975 [DE] Fed. Rep. of Germany ....... 2523633

[51] Int. Cl.$^3$ .................. C07C 127/15; C07C 103/44
[52] U.S. Cl. .................... 560/169; 521/115; 521/129; 521/160; 521/174; 560/159; 564/59; 564/160; 564/197; 564/215
[58] Field of Search ..................... 200/553 R, 561 R; 560/169; 564/59

[56] References Cited

U.S. PATENT DOCUMENTS

| | | | |
|---|---|---|---|
| 2,390,766 | 12/1945 | Zellhoefer | 260/561 R |
| 2,850,529 | 9/1958 | Pinson | 260/482 C |
| 2,851,466 | 9/1958 | Fancher | 260/561 R |
| 3,234,153 | 2/1966 | Britain | 260/247.2 A |
| 3,243,389 | 3/1966 | Moller | 260/482 C |
| 3,784,599 | 1/1974 | Jefferies | 260/482 C |

FOREIGN PATENT DOCUMENTS

| | | |
|---|---|---|
| 559711 | 3/1944 | United Kingdom . |
| 680476 | 10/1952 | United Kingdom . |
| 755848 | 8/1956 | United Kingdom . |
| 755918 | 8/1956 | United Kingdom . |
| 774017 | 5/1957 | United Kingdom . |
| 805575 | 12/1958 | United Kingdom . |
| 1037376 | 7/1966 | United Kingdom . |
| 1249477 | 10/1971 | United Kingdom . |
| 1380016 | 1/1975 | United Kingdom . |
| 1431078 | 4/1976 | United Kingdom . |

OTHER PUBLICATIONS

Chem. Abst. 70:28589t (1969).
Chem. Abst. 75:110033a (1971).
Chem. Abst. 52:15,547e–15549c (1958).
Chem. Abst. 73:85625n (1970).

*Primary Examiner*—Michael L. Shippen
*Attorney, Agent, or Firm*—Gene Harsh; Joseph C. Gil

[57] ABSTRACT

The instant invention is directed to novel compounds and the use thereof in producing polyurethane resins. The compounds generally correspond to the following formula:

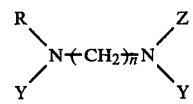

wherein
n is an integer of from 1 to 5,
R is a $C_1$–$C_5$ alkyl group
Y is a $C_1$–$C_5$ alkyl group or a

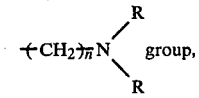 group, and
Z is a

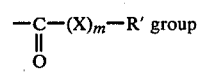 group where n=0 or 1,
X is —O— or

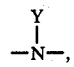

and
R′ is an aliphatic group having from 1 to 15 carbon atoms and may contain ester, ether, or amide groups or tertiary nitrogen and, when m=0, R′ may be a hydrogen atom.

2 Claims, No Drawings

ODORLESS CATALYSTS FOR THE SYNTHESIS OF POLYURETHANES

This is a continuation, of application Ser. No. 685,865 filed May 12, 1976 now abandoned.

BACKGROUND OF THE INVENTION

Polyurethane foams with a wide variety of physical properties have long been produced on a technical scale by the isocyanate polyaddition process from compounds containing several active hydrogen atoms, and in particular compounds containing hydroxyl and/or carboxyl groups, polyisocyanates and water and/or organic blowing agents with the optional addition of catalysts, emulsifiers and other additives [Angew. Chem. A, 59 (1948), page 257]. With suitable choice of components, it is possible by this process to obtain either elastic or rigid foams or any variations between these extremes.

Polyurethane foams are preferably produced by mixing the liquid components. The starting materials which are to be reacted together are either all mixed together at once or an isocyanate prepolymer is first prepared from polyols and an excess of polyisocyanates, and this prepolymer is then foamed.

Tertiary amines have proved to be very suitable catalysts for the production of polyurethane foams, mainly because they accelerate both the reaction between the hydroxyl and/or carboxyl groups and the isocyanate groups and the reaction between water and isocyanate groups. In the one-shot process, the velocities of these reactions, which take place side by side, may be adjusted to each other.

Additional cross-linking reactions accompany the foaming process to form allophanate, biuret and cyanurate structures. In view of the complexity of the reactions, the catalysts must be suitably chosen to ensure that, on the one hand, the various reactions will be synchronized and that, on the other hand, the catalyst will not be fixed too early in the process by being incorporated in the foam and will not subsequently accelerate hydrolytic degradation of the finished foam. Furthermore, the unpleasant odor of many of the tertiary amines frequently used in practice is a disadvantage if they are to be used in the production of foams.

In U.S. Pat. No. 3,243,389, and German Offenlegungsschrift No. 2,354,952, tertiary amines which contain Zerewitinoffactive hydrogen atoms are described as catalysts for isocyanate polyaddition reactions. However, these compounds are gradually built into the polymer structure in the course of the foaming process. They are therefore no longer available at sufficiently high concentrations in the final stages of the reactions, especially in the marginal zone of the foams. This insufficiency adversely affects the surface characteristics and the gelling properties of the polyurethane foams.

DESCRIPTION OF THE INVENTION

The present invention relates to a process for the production of polyurethane resins, and preferably polyurethane foams, by the reaction of (a) compounds which contain at least two hydrogen atoms capable of reacting with isocyanates and which have molecular weights of from 400 to 10,000, (b) polyisocyanates, and (c) optionally, chain lengthening agents, water and/or organic blowing agents, in the presence of catalysts which contain tertiary nitrogen atoms, which process is characterized in that the catalysts used are acyl compounds corresponding to the following general formula:

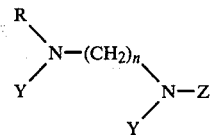

wherein n represents an integer of from 1 to 5, and preferably 2 or 3,

R represents a $C_1$-$C_5$ alkyl group, and preferably methyl or ethyl,

Y represents a $C_1$-$C_5$ alkyl group or the group

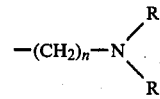

and

Z represents the group

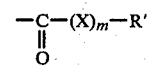

wherein m=0 or 1,

X represents —O— or

and

R' represents an aliphatic group having from 1 to 15 carbon atoms which may contain ester, ether or amide groups or tertiary nitrogen atoms, or where m=O, R' may represent hydrogen.

Z preferably represents one of the following groups:

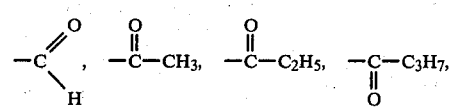

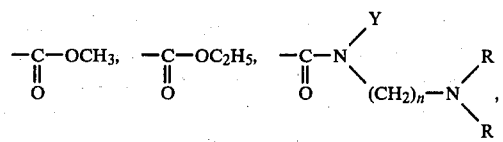

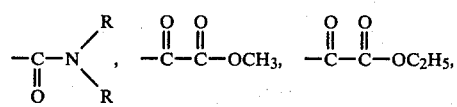

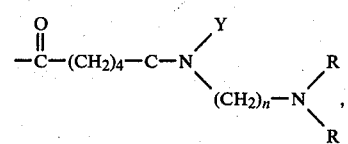

-continued

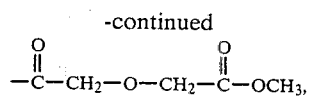

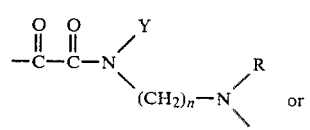

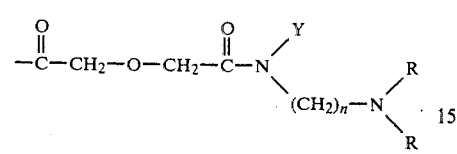

The present invention relates also to compounds corresponding to the following general formula:

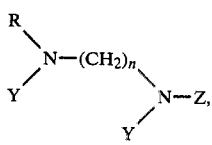

where n, Y, R and Z are as defined above.

The catalysts used according to the present invention may be prepared in a known manner by the reaction of known amines corresponding to the following general formula:

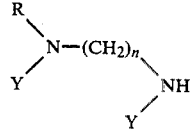

wherein n, R and Y are as defined above; with acylating agents, such as carbon monoxide, carboxylic acids, acid amides, acid esters, acid anhydrides, chlorocarbonic acid esters, dialkyl or diaryl carbonates or dicarbonic acid diesters, and the like.

The catalysts used according to the present invention are distinguished by their surprisingly powerful accelerating effect on the foaming process and by the fact that foams produced therefrom are odorless and have a surprisingly high resistance to hydrolysis. The compounds according to the present invention do not contain any active hydrogen atoms and therefore are not built into the polyurethane via main valency bonds, but remain active during the entire foaming process. The following are typical examples of the catalysts used according to the present invention:

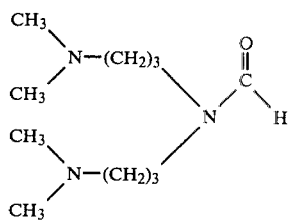 (A)

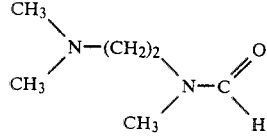 (B)

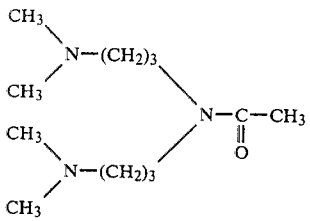 (C)

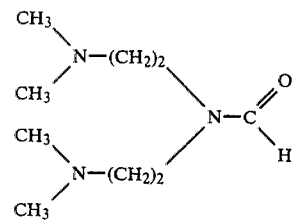 (D)

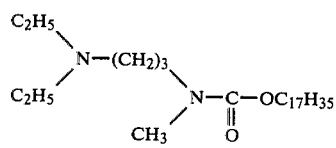 (E)

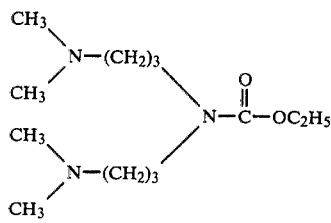 (F)

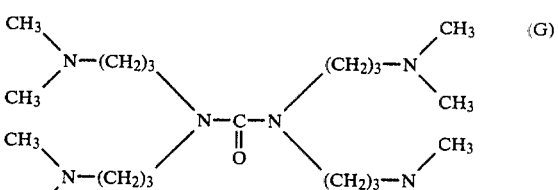 (G)

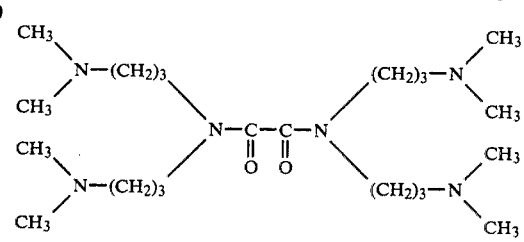 (H)

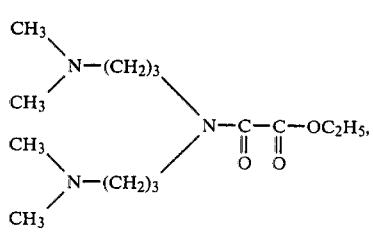 (I)

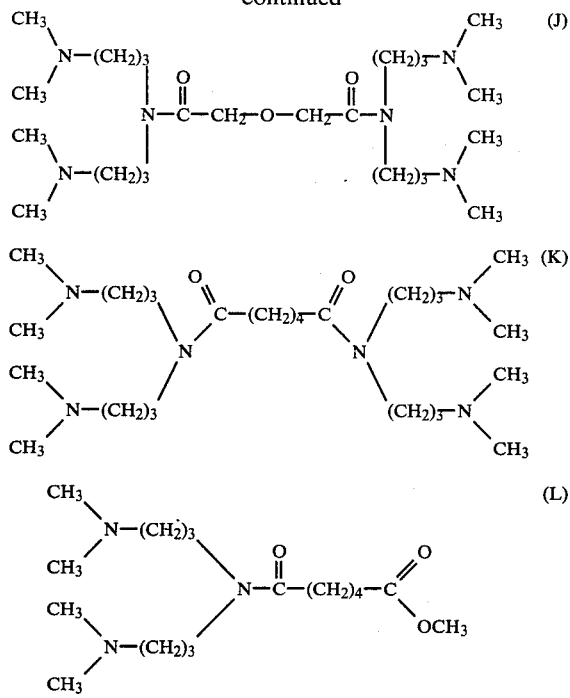

Compounds (A), (C), (F), (G) and (J) are preferred catalysts.

The catalysts used according to the present invention are generally used in quantities of from 0.01 to 5 percent by weight and preferably from 0.1 to 1 percent, by weight, based on the foamable reaction mixture.

The starting components to be used according to the present invention include compounds containing at least two hydrogen atoms capable of reacting with isocyanates and generally having molecular weights of from 400 to 10,000. These not only include compounds containing amino groups, thiol groups or carboxyl groups, but also include polyhydroxyl compounds (which are preferable) and, in particular compounds containing from 2 to 8 hydroxyl groups and especially those having molecular weights of from 800 to 10,000 and most preferably from 1000 to 6000. Examples of such polyhydroxyl materials include polyesters, polyethers, polythioethers, polyacetals, polycarbonates and polyester amides containing at least 2, generally from 2 to 8, and preferably from 2 to 4 hydroxyl groups, of the type generally known for the production of homogeneous and cellular polyurethanes.

Suitable polyesters with hydroxyl groups include, the reaction products of polyhydric, (preferably dihydric) alcohols with the optional addition of trihydric alcohols, and polybasic (preferably dibasic) carboxylic acids. Instead of free polycarboxylic acids, the corresponding polycarboxylic acid anhydrides or esters of lower alcohols or mixtures thereof may be used for preparing the polyesters. The polycarboxylic acids may be aliphatic, cycloaliphatic, aromatic and/or heterocyclic and may be substituted, e.g. by halogen atoms, and/or be unsaturated. The following are mentioned as examples: succinic acid; adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride; tetrachlorophthalic anhydride; endomethylene tetrahydrophthalic acid anhydride; glutaric acid anhydride; maleic acid; maleic acid anhydride; fumaric acid; dimeric and trimeric fatty acids, such as oleic acid, optionally mixed with monomeric fatty acids; dimethylterephthalate; bis-glycol terephthalate; and the like. The following are examples of suitable polyhydric alcohols: ethylene glycol; propylene-1,2- and -1,3-glycol; butylene-1,4- and 2,3-glycol; hexane-1,6-diol; octane-1,8-diol; neopentyl glycol; cyclohexane dimethanol (1,4-bis-hydroxymethylcyclohexane); 2-methyl-propanediol-(1,3); glycerol; trimethylolpropane; hexane-1,2,6-triol; butane-1,2,4-triol; trimethylolethane; pentaerythritol; quinitol; mannitol; sorbitol; methyl glycoside; diethylene glycol; triethylene glycol; tetraethylene glycol; polyethylene glycols; dipropylene glycol; polypropylene glycols; dibutylene glycol; polybutylene glycols; and the like. The polyesters may also contain carboxyl end groups. Polyesters of lactones; such as ε-caprolactone, or hydroxycarboxylic acids, e.g. ω-hydroxycaproic acid, may also be used.

The polyethers used according to the present invention, which contain at least two, generally from 2 to 8 and preferably 2 or 3 hydroxyl groups are also known and may be prepared, for example, by the polymerization of epoxides, such as ethylene oxide, propylene oxide, butylene oxide, tetrahydrofuran, styrene oxide or epichlorohydrin, either alone for example in the presence of $BF_3$, or by the addition of these epoxides, if desired as mixtures or successively, to starting components which contain reactive hydrogen atoms, such as water, alcohols, or amines. Examples of alcohols and amines include: ethylene glycol, propylene-1,3- or -1,2-glycol, trimethylolpropane, 4,4'-dihydroxydiphenylpropane, aniline, ammonia, ethanolamine and ethylene diamine. Sucrose polyethers such as those described in German Auslegeschriften Nos. 1,176,358 and 1,064,938, may also be used according to the present invention. In many cases, it is preferred to use polyethers which contain predominant amounts of primary OH groups (up to 90% by weight based on all the OH groups present in the polyether). Polyethers modified by vinyl polymers are also suitable, for example, the compounds obtained by the polymerization of styrene or acrylonitrile in the presence of polyethers (U.S. Pat. Nos. 3,383,351; 3,304,273; 3,523,093 and 3,110,695 and German Patent No. 1,152,536). Polybutadienes containing OH groups may also be used.

Suitable polythioethers include, in particular, the condensation products obtained by the condensation of thiodiglycol on its own and/or with other glycols, dicarboxylic acids, formaldehyde, aminocarboxylic acids or aminoalcohols. The products obtained are polythio mixed ethers, polythio ether esters or polythioether ester amides, depending on the cocomponents.

Suitable polyacetals include, for example, the compounds prepared from glycols (such as diethylene glycol, triethylene glycol, 4,4'-dioxethoxy-diphenyldimethylmethane and hexanediol) with formaldehyde. Polyacetals suitable for the purpose of the present invention may also be prepared by the polymerization of cyclic acetals.

Suitable polycarbonates with hydroxyl groups are known and include those which may be obtained by the reaction of diols (such as propane-1,3-diol, butane-1,4-diol and/or hexane-1,6-diol, diethylene glycol, triethylene glycol or tetraethylene glycol) with diarylcarbonates (e.g. diphenylcarbonate) or phosgene.

The polyester amides and polyamides which may be used include, for example, the predominantly linear condensates obtained from polybasic saturated and unsaturated carboxylic acids or the anhydrides thereof and polyvalent saturated and unsaturated amino alcohols, diamines, polyamines and mixtures thereof.

Polyhydroxyl compounds already containing urethane groups or urea groups and modified or unmodified natural polyols, such as castor oil, carbohydrates or starch, may also be used. Addition products of alkylene oxides and phenol-formaldehyde resins or alkylene oxides and urea-formaldehye resins are also suitable for the purpose of the present invention.

Representatives of these compounds which are to be used according to the present invention are known and have been described, for example, in High Polymers, Vol. XVI, "Polyurethanes, Chemistry and Technology", by Saunders-Frisch, Interscience Publishers, New York, London, Volume I, 1962, pages 32–42 and pages 44–54 and Vol. II, 1964, pages 5–6 and 198–199 and in Kunststoff-Handbuch, Volume VII, Vieweg-Höchtlen, Carl-Hanser-Verlag, Munich, 1966, on pages 45 to 71.

One may, of course, also use mixtures of the above-mentioned compounds which have molecular weights of from 400 to 10,000 and contain at least two hydrogen atoms capable of reacting with isocyanates, such as mixtures of polyethers and polyesters.

Starting components which may optionally also be used according to the present invention include compounds having molecular weights of from 32 to 400 which contain at least two hydrogen atoms capable of reacting with isocyanates. These also are compounds which contain hydroxyl groups and/or amino groups and/or thiol groups and/or carboxyl groups and preferably hydroxyl groups and/or amino groups, and they serve as chain lengthening agents or cross-linking agents. They generally contain from 2 to 8 hydrogen atoms which are reactive with isocyanates, and preferably contain 2 or 3 hydrogen atoms. The following are mentioned as examples of such compounds: ethylene glycol, propylene-1,2- and -1,3-glycol, butylene-1,4- and -2,3-glycol, pentane-1,5-diol, hexane-1,6-diol, octane-1,8-diol, neopentyl glycol, 1,4-bis-hydroxymethyl-cyclohexane, 2-methyl-1,3-propanediol, glycerol, trimethylolpropane, hexane-1,2,6-triol, trimethylolethane, pentaerythritol, quinitol, mannitol and sorbitol, diethylene glycol, triethylene glycol, tetraethylene glycol, polyethylene glycols having a molecular weight of up to 400, dipropylene glycol, polypropylene glycols having a molecular weight of up to 400, dibutylene glycol, polybutylene glycols having a molecular weight of up to 400, 4,4'-dihydroxydiphenyl propane, di-hydroxymethyl-hydroquinone, ethanolamine, diethanolamine, triethanolamine, 3-aminopropanol, ethylene diamine, 1,3-diaminopropane, 1-mercapto-3-aminopropane, 4-hydroxy- or 4-amino-phthalic acid, succinic acid, adipic acid, hydrazine, N,N'-dimethylhydrazine and 4,4'-diaminodiphenylmethane.

Here again, mixtures of various compounds which have molecular weights of from 32 to 400 and contain at least two hydrogen atoms capable of reacting with isocyanates may be used.

The starting isocyanates used according to the present invention include aliphatic, cycloaliphatic, araliphatic, aromatic and heterocyclic polyisocyanates, such as those described, for example, by W. Siefken in Justus Liebigs Annalen der Chemie, 562, pages 75 to 136.

Examples include ethylene diisocyanate; tetramethylene-1,4-diisocyanate; hexamethylene-1,6-diisocyanate; dodecane-1,12-diisocyanate; cyclobutane-1,3-diisocyanate; cyclohexane-1,3- and -1,4-diisocyanate and mixtures of these isomers; 1-isocyanato-3,3,5-trimethyl-5-isocyanatomethylcyclohexane (German Auslegeschrift No. 1,202,785, U.S. Pat. No. 3,401,190); hexahydrotoly-lene-2,4- and -2,6-diisocyanate and mixtures of these isomers; hexahydrophenylene-1,3- and/or -1,4-diisocyanate; perhydrodiphenylmethane-2,4'- and/or 4,4'-diisocyanate; phenylene-1,3- and -1,4-diisocyanate; tolylene-2,4- and -2,6-diisocyanate and mixtures of these isomers; diphenylmethane-2,4'- and/or -4,4'-diisocyanate; naphthylene-1,5-diisocyanate; triphenylmethane-4,4',4''-triisocyanate; polyphenyl-polymethylene polyisocyanates, which may be obtained by aniline-formaldehye condensation followed by phosgenation and which have been described, for example, in British Patent Nos. 874,430 and 848,671; m- and p-isocyanatophenyl-sulphonylisocyanates as described in U.S. Pat. No. 3,454,606; perchlorinated aryl polyisocyanates, such as the compounds described in U.S. Pat. No. 3,277,138; polyisocyanates containing carbodiimide groups as described in U.S. Pat. No. 3,152,162; the diisocyanates described in U.S. Pat. No. 3,492,330; polyisocyanates containing allophanate groups as described, for example, in British Patent No. 994,890, Belgian Patent No. 761,626 and published Dutch Patent Application No. 7,102,524; polyisocyanates containing isocyanurate groups as described, for example, in U.S. Pat. No. 3,001,973, in German Pat. Nos. 1,022,789; 1,222,067 and 1,027,394 and in German Offenlegungsschriften No. 1,929,034 and 2,004,048; polyisocyanates containing urethane groups as described in Belgian Patent No. 752,261 or in U.S. Pat. No. 3,394,164; polyisocyanates containing acylated urea groups as described in German Patent No. 1,230,778; polyisocyanates containing biuret groups as described in U.S. Pat. Nos. 3,124,605 and 3,201,372 and in British Patent No. 889,050; polyisocyanates prepared by telomerization reactions as described in U.S. Pat. No. 3,644,106; polyisocyanates containing ester groups, such as those described in British Patent Nos. 965,474 and 1,072,956, in U.S. Pat. No. 3,567,763 and in German Patent No. 1,231,688; reaction products of the above-mentioned isocyanates with acetals as described in German Patent No. 1,072,385; and polyisocyanates containing polymeric fatty acid residues as described in U.S. Pat. No. 3,455,883.

The distillation residues obtained from commercial production of isocyanates and still containing isocyanate groups may also be used, if desired as solutions in one or more of the above-mentioned polyisocyanates. Mixtures of the above-mentioned polyisocyanates may also be used.

As a rule, it is particularly preferred to use readily available polyisocyanates such as tolylene-2,4- and -2,6-diisocyanate and mixtures of these isomers ("TDI"); polyphenyl-polymethylene polyisocyanates which may be prepared by aniline-formaldehyde condensation followed by phosgenation ("crude MDI"); and, polyisocyanate containing carbodiimide groups, urethane groups, allophanate groups, isocyanurate groups, urea groups or biuret groups ("modified polyisocyanates").

According to the present invention, water and/or readily volatile organic substances may be added as blowing agents. Suitable organic blowing agents include: acetone, ethyl acetate; halogenated alkanes, such as methylene chloride, chloroform, ethylidene chloride, vinylidene chloride, monofluorotrichloromethane, chlorodifluoromethane and dichlorodifluoromethane; butane; hexane; heptane; diethyl ether; and the like. Compounds which decompose at temperatures above room temperature to liberate gases, such as nitrogen, may also act as blowing agents. Examples include azo compounds, such as azoisobutyric acid nitrile. Other examples of blowing agents and details concerning the use of blowing agents may be found in Kunststoff-Handbuch, Volume VII, published by Vieweg and Höchtlen, Carl-Hanser-Verlag, Munich 1966, on pages 108 and 109, 453 to 455 and 507 to 510.

Known catalysts may, of course, be used in addition to the compounds according to the present invention.

Surface active additives, such as emulsifiers and foam stabilizers, may also be used according to the present invention. Suitable emulsifiers are, for example, the sodium salts of castor oil sulphonates or salts of fatty acids with amines, such as oleic acid diethylamine or stearic acid diethanolamine. Alkali metal or ammonium salts of sulphonic acids, such as dodecylbenzenesulphonic acid or dinaphthylmethane disulphonic acid, or of fatty acids, such as ricinoleic acid, or of polymeric fatty acids, may also be used as surface active additives.

Particularly suitable foam stabilizers are the polyether siloxanes, especially those which are water-soluble. The structure of these compounds is generally such that a copolymer of ethylene oxide and propylene oxide is connected to a polydimethylsiloxane group. Foam stabilizers of this type have been described in U.S. Pat. Nos. 2,834,748; 2,917,480 and 3,629,308.

According to the present invention, the following substances may also be added: reaction retarders, e.g. compounds which are acid in reaction, such as hydrochloric acid or organic acid halides; known cell regulators such as paraffins or fatty alcohols or dimethylpolysiloxanes; pigments or dyes; flame retarding agents, such as trischloroethylphosphate, tricresylphosphate or ammonium phosphate or polyphosphate; stabilizers against ageing and weathering; plasticizers, fungistatic and bacteriostatic substances; and fillers, such as barium sulphate, kieselguhr, carbon black or whiting.

Other examples of surface active additives, foam stabilizers, cell regulators, reaction retarders, stabilizers, flame retarding substances, plasticizers, dyes, fillers and fungistatic and bacteriostatic substances which may also be used according to the present invention, as well as methods of using them and their mode of action have been described in Kunststoff-Handbuch, Volume VII, published by Vieweg and Höchtlen, Carl-Hanser-Verlag, Munich 1966, on pages 103 to 113.

According to the present invention, the starting materials are reacted together by the known one-shot process, prepolymer process or semi-prepolymer process, in many cases using mechanical devices, such as those described in U.S. Pat. No. 2,764,565. Details concerning processing apparatus which may also be used according to the present invention may be found in Kunststoff-Handbuch, Volume VII, published by Vieweg and Höchtlen, Carl-Hanser-Verlag, Munich, 1966, pages 121 to 205.

According to the present invention, production of foams is in many cases carried out by the process of foaming in the mold. In this process, the reaction mixture is introduced into a mold made of a metal, (e.g. aluminum) or of plastic (e.g. an epoxide resin) in which it foams to form the shaped product. This process of foaming in the mold may be carried out to produce a product with a cellular structure on its surface or it may be carried out so that the product has a compact skin and cellular core. According to the present invention, either result may be achieved by either introducing just sufficient foamable reaction mixture into the mold or by introducing a larger quantity of reaction mixture than is necessary for filling the interior of the mold with foam. The latter method is known as "overcharging". A procedure for carrying it out has been disclosed, for example, in U.S. Pat. Nos. 1,178,490 and 3,182,104.

The process of foaming in the mold is in many cases carried out with the aid of so-called "external mold release agents" which are known, such as silicon oils, but so-called "internal mold release agents" may also be used, if desired as mixtures with external mold release agents, for example, those disclosed in German Offenlegungsschriften Nos. 1,121,670 and 2,307,589.

Cold setting foams may also be produced according to the present invention (see, e.g., British Patent No. 1,162,517, German Offenlegungsschrift No. 2,153,086).

The foams may, of course, be produced by a process of block foaming or by the known double conveyor belt process.

The products of the process are flexible, semiflexible or hard foam resins which contain urethane groups. They are used for the conventional purposes of such products as mattresses and upholstery material for the furniture and motor car industry, for the manufacture of protective padding of the type used in the motor car industry and as insulating materials in general and for insulation against cold or heat in particular in the building industry or the refrigeration industry.

The following Examples illustrate the invention without restricting it.

(Unless otherwise indicated, the quantities given are parts by weight or percentages by weight).

EXAMPLE 1

450 grams(10 mol) of formamide are introduced into a 2 liter three-necked flask and heated to 15° C. 935 g (5 mol) of N,N-bis-(3-dimethyl-amino-n-propyl)-amine (92% pure according to gas chromatography) are then added with stirring in the course of one hour. Vigorous evolution of ammonia occurs at once. Heating is continued for 3½ hours after all the amine has been added. At the end of this time, none of the original amine may be detected. 966 g of the following compound are obtained by distillation:

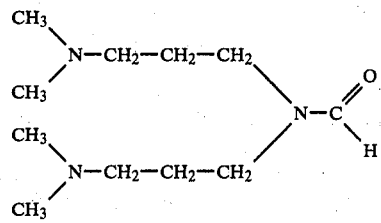

(=97.9%, based on the amine of the given degree of purity used as starting material).

Bp$_{0.19\ mm}$=125° to 126° C.

purity (determined by gas chromatography)=99.2%.

The identity of the compound as N,N-bis-3-dimethylamino-n-propyl-formamide is confirmed by its IR and NMR spectra and by elemental analysis.

EXAMPLE 1a

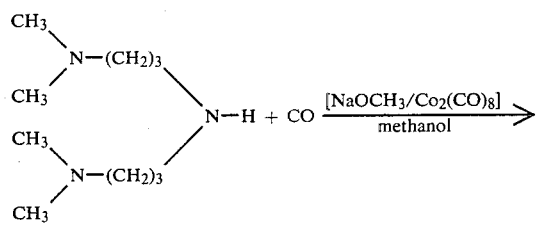

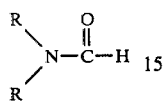

2 g of sodium methylate and 1 g of dicobalt octacarbonyl dissolved in 7 ml of toluene are added to 93.5 g (0.5 mol) of N,N-bis-(3-dimethylamino)-n-propylamine (purity according to GC: 87%) dissolved in 700 ml of methanol. This mixture is reacted with carbon monoxide at a pressure of 200 bar and a temperature of 125° C. for 2 hours. When the mixture has been cooled to room temperature it is filtered. The methanol is then drawn off and the product distilled. Yield: 58.5 g (62.5% of the theoretical yield, based on amine which is 87% pure).

EXAMPLE 2

2040 g (20 mol) of acetic acid anhydride are introduced into a 5 liter three-necked flask and heated to 80° C. 1870 g of N,N-bis-(3-dimethylamino-n-propyl)-amine (degree of purity 87% according to GC) are introduced dropwise in the course of 2 hours with stirring. The reaction temperature should rise to a maximum of 90° C. during this time. Stirring is continued for 6 hours at 90° C. and the excess anhydride and the acetic acid formed in the reaction are then distilled off over a distillation column at 0.28 Torr, the temperature at this stage rising from 90° C. to 120° C. The main fraction is finally collected at from 120° to 122° C. and 0.28 Torr (1954 g).

Redistillation of the main fraction after removal of 22.5 g of the preceding fraction yields 1867 g (93.5% of the theoretical yield at the given degree of purity of the amine) of pure di-3-dimethylamino-n-propyl-acetamide, B.p.$_{0.28}$ mm = 120° to 121° C.

Purity according to GC = 99.8%.

The identity of the compound is confirmed by the IR and NMR spectra and by elemental analysis.

EXAMPLE 3

528 g (5.17 mol) of acetic acid anhydride are gradually added to 300 g (2.59 mol) of 1-dimethylamino-3-methylamino-propane at 80° C. and the mixture is then stirred for 15 hours at 135° C. Acetic acid and excess acetic acid anhydride are then distilled off in a waterjet vacuum until the temperature indicated on the transition thermometer is 65° C. The reaction mixture is cooled to room temperature, mixed with 700 ml of acetone, neutralized with potassium carbonate and filtered. The solvent is removed using a rotary evaporator and the residue is distilled in a high vacuum.

Yield: 313 g = 76.6% of the theoretical yield of N-methyl-N-(3-dimethylamino-propyl)-acetamide:

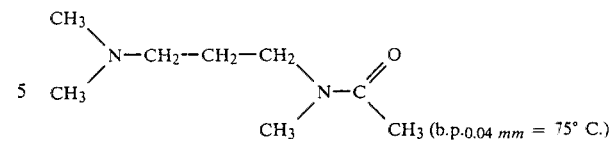

Calculated: C, 60.7; H, 11.4; N, 17.72. Observed: C, 60.7; H, 11.5; N, 18.0.

EXAMPLE 4

270 g (2.64 mol) of acetic acid anhydride are gradually added to 210 g (1.32 mol) of N-dimethyl-N'-methyl-N''-methyl-diethylenetriamine at 80° C. at the mixture is maintained at the reflux temperature for 6 hours. The product is worked-up as described in Example 3. Yield: 176 g (66.3% of the theoretical yield) of N-dimethyl-N'-methyl-N''-acetyl-diethylenetriamine:

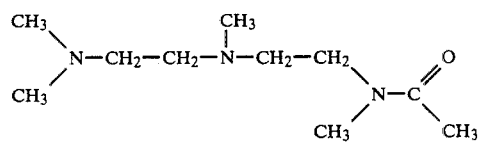

Calculated: C, 59.7; H, 11.45; N, 20.9. Observed: C, 59.4; H, 11.4; N, 20.7.

The IR and NMR spectra prove the identity of the compound.

EXAMPLE 5

178.2 g (1.1 mol) of diethyldicarbonate are added to 187 g of N,N-bis-(3-dimethylamino-n-propyl)-amine (degree of purity 87.6%) in an apparatus equipped with stirrer, condenser, thermometer and dropping funnel in the course of 22 minutes while the temperature is maintained at 40° C. by means of an ice bath. Evolution of carbon dioxide sets in when about one third of the acylating agent has been added and it is completed quantitatively within 12 minutes. Stirring is then continued for 30 minutes at 40° C. 35 g of ethanol are distilled off in a water-jet vacuum and 227 g of 0.2 Torr and a temperature of from 95° to 105° C. On redistillation, this distillate yields 183 g of purest N,N-bis-(dimethyl-amino-n-propyl)carbamic acid ethyl ester:

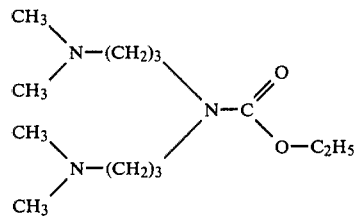

(= 80.7% of the theoretical yield). The structure of the compound is confirmed by the IR and NMR spectra and by elemental analysis.

EXAMPLE 6

118 g (1 mol) of diethylcarbonate and 4 g of sodium methylate are added to 374 g (2 mol) of N,N-bis-(3-dimethylamino-n-propyl)-amine (degree of purity 99.8%). The reaction mixture is maintained at 160° C. for one hour and then at 200° C. for 1.5 hours, during which time the ethanol distills off. The reaction mixture is left to cool and 18 g of solid is isolated by suction filtration. The filtrate clearly shows urethane and urea carbonyl vibrations ($\gamma_{CO}=1700$ cm$^{-1}$ and 1620 to 1630 cm$^{-1}$). The constituents are separated using a thin layer evaporator. The distillate obtained at 160° C./0.4 Torr contains 278 g of the urethane according to Example 5 and amine used as starting material. 90 g (22.3% of the theoretical yield) of tetra-3-dimethylamino-n-propyl-urea:

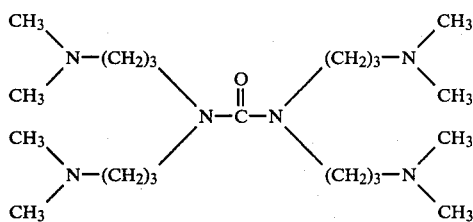

are left as residue. The structure of the compound was confirmed by the IR spectra and by titration of the basic nitrogen with perchloric acid in glacial acetic acid.

EXAMPLE 7

The following components were reacted:

100 parts, by weight, of a polypropylene glycol which had been started on trimethylolpropane and modified with ethylene oxide so that it finally contained 60% of primary hydroxyl end groups and had an OH number of 35, 2.5 parts, by weight, of water, 0.6 parts, by weight, of diazabicyclo-2,2,2-octane, 1.0 parts, by weight, of triethanolamine, 1.0 part, by weight, of siloxane 1 from German Offenlegungsschrift 2,221,811, 0.3 parts, by weight, of the catalyst according to Example 1 and 41.4 parts, by weight, of an isocyanate mixture consisting of 40%, by weight, of a tolylene diisocyanate mixture (2,4- and 2,6-isomers in proportions of 65:35) and 60%, by weight, of a crude polyphenyl-polymethylene-polyisocyanate (viscosity about 200 cP at 25° C.). The polyphenyl-polymethylene-polyisocyanate had been obtained by aniline-formaldehyde condensation followed by phosgenation.

A foam with the following mechanical properties is obtained:

| Gross density | DIN 53420 (kg/m$^3$) | 45 |
| Tension test | DIN 53571 (KPa) | 60 |
| Elongation at break | DIN 53571 (%) | 80 |
| Compression test | DIN 53577 (KPa) | 2.0 |

EXAMPLE 8

100 parts, by weight, of a polypropylene glycol which has been started on trimethylolpropane and modified with ethylene oxide to result in 60% of primary hydroxyl end groups and an OH number of 28 are reacted with 3.2 parts, by weight, of water, 0.15 parts, by weight of diazabicyclo-2,2,2-octane, 1.0 part, by weight, of siloxane 1 from German Offenlegungsschrift 2,221,811, 0.3 parts, by weight, of the catalyst according to Example 2 and 39.0 parts, by weight, of the polyisocyanate described below.

The polyisocyanate was prepared as follows: 20 parts of 1,2-propylene glycol are added to a mixture of 225 parts of a mixture of 80% of 2,4- and 20% of 2,6-tolylene diisocyanate and 274 parts of 4,4'-diphenylmethane diisocyanate at 60° C. and reacted for 30 minutes. The mixture is heated to 130° C. after the addition of 1 part of β-phenylethyl-ethyleneimine. Trimerization which takes place at this temperature is stopped after 2½ hours, when the reaction mixture has an isocyanate content of 26.5%, by weight, by the addition of 1 part of p-toluenesulphonic acid methyl ester.

After dilution with 624 parts of the mixture of 2,4- and 2,6-tolylene diisocyanate, a polyisocyanate solution which has the following characteristics are obtained: NCO%, by weight, =38.4; viscosity at 25° C.=24 cP; $n_D^{50}=1.5738$.

A foam with the following mechanical properties is obtained:

| Gross density | DIN 53420 (kg/m$^3$) | 38 |
| Tension test | DIN 53571 (KPa) | 80 |
| Elongation at break | DIN 53571 (%) | 145 |
| Compression test | DIN 53577 (KPa) | 2.5 |

EXAMPLE 9

50 parts, by weight, of a polypropylene glycol which has been started on trimethylolpropane and modified with ethylene oxide so that it finally contains 60% of primary hydroxyl end groups and has an OH number of 28 and 50, parts by weight, of a polypropylene glycol which has been started on trimethylolpropane and modified with ethylene oxide so that it finally contains 70% of primary hydroxyl end groups and which has also been grafted with acrylonitrile and styrene in proportions of 60:40 and has an OH number of 28, 2.7 parts, by weight, of water, 0.15 parts, by weight, of diazabicyclo-2,2,2-octane, 0.08 parts, by weight, of 2,2'-dimethylaminodiethylether, 1.0 part, by weight, of siloxane 1 from German Offenlegungsschrift No. 2,221,811, 0.1 part, by weight, of a polyether polysiloxane which is marketed by TH. Goldschmidt AG of Essen, BRD, under the trade name "Tegostab B 2909", 0.6 parts, by weight, of the catalyst according to Example 1, 34.0 parts, by weight, of a tolylene diisocyanate mixtures (2,4- and 2,6-isomers in proportions, by weight, of 80:20) and 20.0 parts, by weight, of a polyphenyl-polymethylene polyisocyanate which has been obtained by aniline-formaldehyde condensation followed by phosgenation are reacted together in a mold.

A molded foam with the following mechanical properties is obtained:

| Gross density | DIN 53420 (kg/m$^3$) | 43 |
| Tension test | DIN 53571 (KPa) | 170 |
| Elongation at break | DIN 53571 (%) | 170 |
| Compression test | DIN 53577 (KPa) | 4.1 |

EXAMPLE 10

50 parts, by weight, of a polypropylene glycol which has been started on trimethylolpropane and modified with ethylene oxide to results in 60% of primary hydroxyl end groups and an OH number of 28, 50 parts, by weight, of a polypropyleneglycol which has been started on trimethylolpropane and modified with ethylene oxide to result in 70% of primary hydroxyl end groups and which has been grafted with acrylonitrile and styrene in proportions of 60:40 and has an OH number of 28, 2.7 parts, by weight, of water, 1.0 part, by weight, of siloxane 1 from German Offenlegungsschrift No. 2,221,811, 0.1 part, by weight, of a polyether polysiloxane marketed by TH. Goldschmidt AG, Essen BRD, under the trade name "Tegostab B 2909", 2.0 parts, by weight, of the catalyst according to Example 5, 34.0 parts, by weight, of a tolylene diisocyanate mixture (2,4- and 2,6-isomer in proportions, by weight, of 80:20) and 20.0 parts, by weight, of a polyphenyl-polymethylene polyisocyanate which has been obtained by aniline-formaldehyde condensation followed by phosgenation are reacted together in a mold.

A molded foam with the following mechanical properties is obtained:

| Gross density | DIN 53420 (kg/m$^3$) | 42 |
| Tension test | DIN 53571 (KPa) | 160 |
| Elongation at break | DIN 53571 (%) | 150 |
| Compression test | DIN 53577 (KPa) | 3.9 |

EXAMPLE 11

90 g of a polyether having a molecular weight of 4800 which has been prepared by chemical addition of propylene oxide (87%) and ethylene oxide (13%) to trimethylolpropane are mixed with 0.5 g of the compound according to Example 3, 5 g of triethanolamine, 2 g of tall oil and 2.5 g of water.

This mixture and 60 g of a polyphenylpolymethylene polyisocyanate which has been obtained by phosgenation of an aniline-formaldehyde condensate and has an isocyanate content of 31% are vigorously mixed in a mixing head and left to foam in a mold. The resulting foam has the following mechanical properties:

| Density (kg/m$^3$) | 64 |
| Tensile strength (KPa) | 155 |
| Elongation at break (%) | 70 |
| Compression resistance at 40% compression (KPa) | 17.4 |
| Residual pressure deformation (%) at 50% compression | 7 |

EXAMPLE 12

90 g of the polyether mentioned in Example 11, 0.8 g of the compound according to Example 4, 5 g of triethanolamine, 2 g of tall oil and 2.5 g of water are reacted under the conditions indicated in Example 11 with the polyisocyanate used in Example 11.

The resulting foam has the following properties:

| Density (kg/m$^3$) | 61 |
| Tensile strength (KPa) | 145 |
| Elongation at break (%) | 60 |
| Compression resistance at 40% compression (KPa) | 15 |
| Residual pressure deformation (%) at 50% compression | 6 |

EXAMPLE 13

90 g of the polyether mentioned in Example 11, 0.5 g of the compound according to Example 5, 5 g of triethanolamine, 2 g of tall oil and 2.5 g of water are reacted under the conditions indicated in Example 11 with the polyisocyanate used in Example 11. The resulting foam has the following properties:

| Density (kg/m$^3$) | 61 |
| Tensile strength (KPa) | 155 |
| Elongation at break (%) | 60 |
| Compression resistance (KPa) at 40% compression | 16.3 |
| Residual pressure deformation (%) at 50% compression | 7 |

What is claimed is:

1. Compound of the formula:

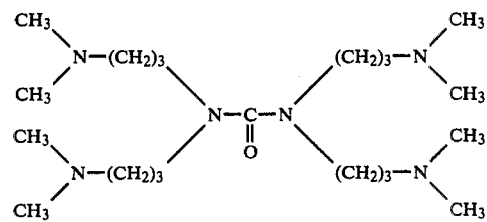

2. Compound of the formula:

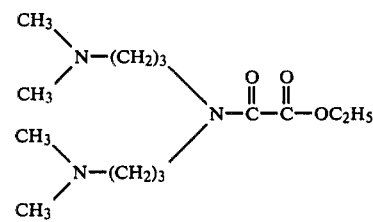

* * * * *